United States Patent [19]

Goble et al.

[11] 3,960,008

[45] June 1, 1976

[54] PILE CAPACITY TESTING MEANS

[76] Inventors: George G. Goble, 18908 Lomond Blvd., Shaker Heights, Ohio 44094; Frank Rausche, 38320 North Lane, Willoughby, Ohio 44094

[22] Filed: Dec. 12, 1974

[21] Appl. No.: 532,050

[52] U.S. Cl. .............................. 73/84; 61/53.64; 61/53.6
[51] Int. Cl.$^2$ ........................................ G01N 3/34
[58] Field of Search ................. 73/84, 88 E, 88 C; 173/20, 1; 61/53.64, 53.6

[56] References Cited
UNITED STATES PATENTS

| | | | |
|---|---|---|---|
| 1,979,547 | 11/1934 | Hood | 61/53.6 |
| 3,190,110 | 6/1965 | Craycraft | 73/12 |
| 3,298,222 | 1/1967 | Costello et al. | 73/84 |
| 3,391,571 | 7/1968 | Johanson | 173/20 |
| 3,470,701 | 10/1969 | Turzillo | 61/53.2 |
| 3,498,388 | 3/1970 | Jovis | 73/84 |
| 3,535,919 | 10/1970 | Budlong et al. | 73/84 |

*Primary Examiner*—James J. Gill
*Assistant Examiner*—Anthony V. Ciarlante
*Attorney, Agent, or Firm*—McNenny, Farrington, Pearne & Gordon

[57] ABSTRACT

A method of constructing cast-in-place concrete piles by which the static load bearing capacity of a pile is dynamically determined during its formation. In the disclosed method, successive charges of concrete are placed into a removable casing and subsequently driven into the soil by a drop hammer. The pile may be of the pedestal type having an enlarged base for increased load capacity. The pile shaft is formed by incrementally elevating the casing and driving concrete into a vertical series of annular enlargements corresponding to the points at which the lower end of the casing is stopped. The load capacity of the pile base and the individual enlargements is determined by measuring the resistance of the soil against penetration of the several concrete portions when driven by the hammer. This resistance is calculated as a product of the total mass of the concrete in motion and the hammer multiplied by the deceleration of the hammer and an adjustment factor to account for the effects of nonaxial concrete motion, energy losses, etc., at or about the time of zero velocity as determined by a decelerometer or any other suitable device mounted on the hammer.

5 Claims, 6 Drawing Figures

PILE CAPACITY TESTING MEANS

BACKGROUND OF THE INVENTION

The invention relates to a method of setting concrete piles and, more specifically, relates to a method of casting concrete piles in place while determining their static load capacity through dynamic measurement.

PRIOR ART

Concrete piles are commonly cast in place and may either be uncased or permanently cased. In the uncased type, a removable casing or form is usually sunk to a desired soil penetration, filled with fresh concrete, and removed from the soil to leave a shaft of concrete in the required length. The removable casing, which may be used to bore through the soil, supports the soil against collapse until the concrete is in place. To increase the end bearing capacity of the pile, concrete is driven out of the lower end of the casing by dropping a hammer on a mass of concrete in the casing.

Successive hammer blows force the concrete expelled from the casing into a bulb shape to produce a pile commonly referred to as a mushroom or pedestal type pile. End bearing capacity of the pile is increased due to the resulting enlargement in end area over that defined by the diameter of the casing. In one form of concrete piles, after a bulb end is formed, the casing is incrementally raised and the hammer is repeatedly dropped to form a succession of vertically spaced enlargements or rings along the pile shaft corresponding to the points at which the casing end stops during its stepped elevation. These axially spaced rings cooperate with surrounding soil to improve the friction bearing capacity of the pile over that which would be produced by a smooth cylindrical exterior.

It is often necessary to determine the axial load capacity or resistance of a pile while or after it is placed so that adequate piling is provided before construction on the pile begins. Among various methods used to test the load capacity of a pile, a common technique is the measurement of the displacement of the pile when struck with a hammer of known energy. Typically with this method, the pile or portion thereof is struck by a hammer of known mass falling a known distance (or with known velocity). A hammer blow causes a set or displacement of the pile into the soil. When the set or displacement is no more than a certain value, determined by calculations involving the energy of the hammer, the pile is assumed to have a satisfactory resistance.

The accuracy of resistance measurement determined by this method is somewhat limited, since it does not measure resistance at the final resting point following the hammer below but measures an average resistance between the initial position and the resting point. Moreover, this average resistance may be velocity dependent and may, therefore, not reflect a true measurement of static resistance. Static testing of piles is generally expensive and time consuming, since a means of developing relatively large forces must be provided. A method of dynamically determining the static capacity of a rigid pile was proposed by Eiber in 1958[1], in which a decelerometer was attached to a steel pile and the capacity was determined as the product of pile mass and pile deceleration at the time of zero velocity. Another method of dynamically determining the static capacity of a rigid pile is disclosed in U.S. Pat. No. 3,535,919 to Budlong et al. According to this patent, signals from an accelerometer and a force transducer secured to the rigid pile are operated on by suitable electronic circuitry to compute the static soil resistance on the pile during each blow of a hammer.

[1] Eiber, R. J., "A Preliminary Laboratory Investigation of the Prediction of Static Pile Resistances in Sand," Master's Thesis, Case Institute of Technology, Cleveland, Ohio, 1958.

SUMMARY OF THE INVENTION

The invention provides a method of dynamically measuring the static load capacity of a pedestal type concrete pile as it is being cast in place, that is, before it has set or hardened to an appreciable degree. The pile is constructed by sinking a removable casing to a required soil penetration and subsequently driving at least a portion of a charge of concrete out of a lower end of the casing with a drop hammer. In accordance with the invention, the hammer is provided with a decelerometer and the mass of the hammer and concrete charge are determined prior to driving. The hammer is dropped on the concrete mass and following the instant of impact, the concrete and hammer are assumed to be moving in unison such that the measured deceleration on the hammer is that of the total mass in the system. The deceleration signal is integrated to determine the instantaneous velocity of the system.

At the point of zero velocity, the corresponding deceleration is that produced by the resistance of the surrounding soil at a static or zero velocity condition. The actual value of the static resistance is derived from the equation $R = M_t A_d$ where $M_t$ is the combined total movable mass of the hammer and charge of concrete and $A_d$ is the deceleration at zero velocity. This computed resistance represents the load bearing capacity of the portion of the pile formed by the initial charge of concrete. Empirically and/or analytically derived factors can be used to adjust the deceleration value in order to account for nonaxial deceleration components of the concrete, plastic and dynamic effects otherwise neglected.

In the preferred embodiment, the initial concrete charge is used to form the base of the pile. This initial charge is driven by one or more blows of the hammer to cause it to expand laterally and develop a bulb of desired load capacity as determined by deceleration measurement. After formation of the base, the casing is raised a limited distance and another charge is introduced into it. The hammer is again dropped to compact this second charge and cause it to be laterally expanded to form an annular ring just below the end of the casing in a manner similar to the base, but to a lesser extent. The hammer deceleration is again measured to determine the soil condition and resistance associated with the second mass of concrete. The procedure of lifting the casing a limited distance, introducing a new charge of concrete into it and driving the charge with the hammer while monitoring deceleration is repeated until the entire shaft of the pile is produced. The outer surface of the pile shaft thereby includes series of annular rings or enlargements which improve the load capacity of the pile.

The invention, in addition to providing advantages normally associated with the use of cast-in-place concrete piles, such as economy and low hammer capacity, thus provides instantaneous measurement of the load bearing capacity of the pile as it is constructed. Such measurement permits substantial savings in construction time and material since unnecessary overdriving may be eliminated in addition to providing an excellent tool to control the pile quality during production. Similarly, the time and expense associated with static load testing are avoided.

DESCRIPTION OF THE PREFERRED EMBODIMENT

Figures 1, 2, 3, 4:
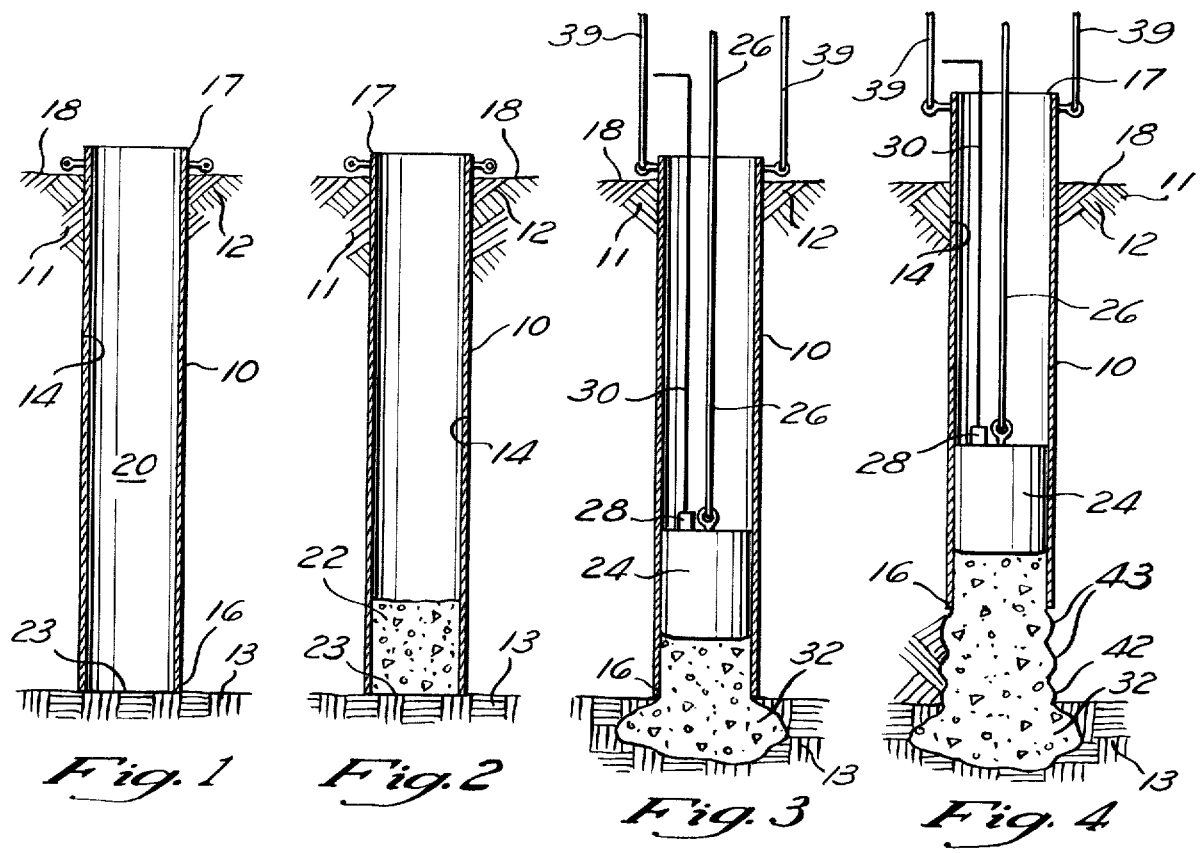
FIG. 1 is an elevational sectional view of a removable pile casing in place at a desired soil depth.
FIG. 2 is a view similar to FIG. 1 illustrating an initial charge of concrete provided in the lower end of the pile casing.
FIG. 3 is a view similar to the preceding figures illustrating a drop hammer in the casing and the formation of a bulbous base of the preferred pile configuration.
FIG. 4 illustrates the pile casing in a partially removed position and formation of a portion of the shaft of the pile.

Referring now to the Figures, a removable casing 10 is set in a hole 14 formed in the earth or soil, broadly indicated at 11, where it is desired to provide bearing support for structure above the soil. The removable casing 10, ideally, is an elongated hollow cylinder formed of metal pipe or similar construction. The pile casing 10 is vertically arranged, but may be inclined where necessary or desired. In the illustrated situation, the soil 11 comprises an upper stratum 12 of relatively low bearing value and an underlying stratum 13 of high bearing value. The stratum 13, on the other hand, may be loose sand capable of being compacted.

A lower end 16 of the casing 10 is positioned on the lower stratum 13 at a depth immediately above the eventual base of the pile. The casing 10 is of sufficient length to provide an upper end 17 above the soil line or ground level 18. Any of a variety of methods is used to sink the casing 10 to the desired depth. These methods include driving the casing through the soil with a hammer and subsequently removing the soil forced into its interior, designated 20. A second method includes the use of a rigid blunt or pointed end cap (not shown) to close off the lower end 16 of the casing 10 as it is driven downwardly by a hammer. This end cap is later displaced from the casing end 16 by concrete forced out of the casing 10 during formation of the pile. In a third method, dry concrete is used as an end plug to keep the casing 10 from filling with soil as it is being driven. In a fourth method, the casing 10 may be driven simultaneously with a mandrel (not shown) in the casing interior 20. The mandrel is used to support the casing 10 from buckling or other failure and to maintain soil out of the casing 10 during placement. The mandrel may be removed after the casing is set. Besides these enumerated techniques, various other methods for positioning the casing 10 are familiar to those skilled in the art.

After the casing is set, as illustrated in FIG. 2, an initial charge 22 of concrete is dropped or otherwise placed in the casing end 16 at the base, designated 23, of the hole 14. A drop hammer 24 of suitable mass, illustrated in FIGS. 3 and 4, is suspended above the casing 10. The drop hammer 24 is of sufficient mass to allow it to drive the initial concrete charge 22 and subsequent charges from the end 16 of the casing into the surrounding soil 11 when dropped from workable heights. The illustrated hammer 22 is movable freely through the casing interior 20 and may be retracted or lifted from the casing by a cable 26. Although a simple drop hammer 24 is illustrated, it will be apparent from the present discussion that other types of hammers or driving means such as a steam hammer of suitable energy capacity may be employed with the invention.

The hammer 24 is dropped one or more times on the initial concrete charge 22 to force the concrete out of the casing end 16 into the high bearing value soil stratum 13. The concrete 22 is caused to penetrate into this lower stratum 13 both vertically and laterally to form a bulb or base 32. The lateral or radial spreading effect at the bulbous base 32 increases the end load bearing capacity of the pile over that which would result from a pile having a diameter equal to the inside diameter of the casing 10 since, when complete, the effective diameter of the base is substantially larger than the casing diameter. Where the casing 10 is provided with an end cap at its lower end 16 to facilitate driving of the casing, the end cap is forced off the casing end 16 into the soil 13 by advancement of the concrete out of the casing 10.

Rigidly mounted on the hammer 24 is a decelerometer 28 adapted to transmit, through an electrical wire circuit 30, a signal indicative of the rate of deceleration of the hammer. The decelerometer 28 is a suitable commercially available unit which, preferably provides a voltage signal proportional to a measured rate of deceleration. The voltage signal transmitted by the wire circuit 30, or any other means of transmittance, is monitored by suitable electronic circuitry which, if desired, drives a recording instrument adapted to plot deceleration as a function of time on a suitable recording medium such as a paper chart. The recording device may be chosen from a number of commercially available units familiar to those skilled in the art.

Figure 5:
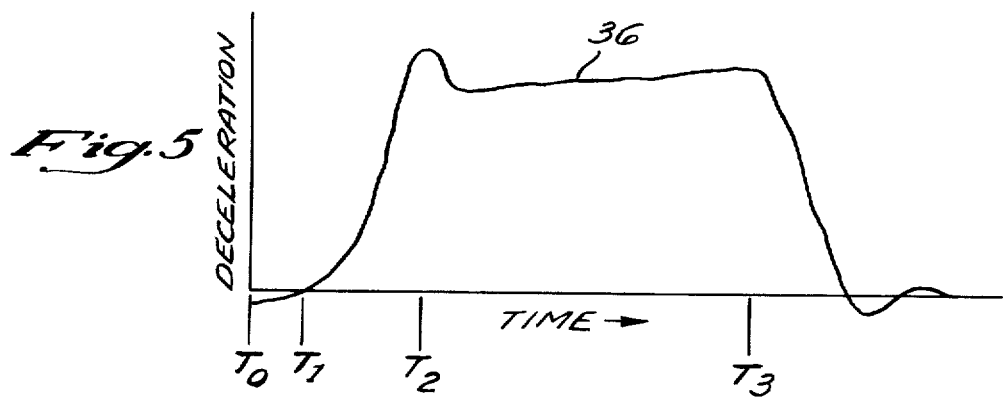
FIG. 5 is a diagrammatic curve representing instantaneous deceleration of the hammer as a function of time.

Instantaneous deceleration of the hammer 24, as sensed by the decelerometer 28, from the instant of impact with the initial and subsequent charges of concrete is illustrated in general form in a curve 36 of FIG. 5. At $T_0$ the hammer has contacted the concrete charge and between $T_0$ and $T_1$ the concrete charge is compacted and a rapid increase in deceleration occurs. The deceleration increases from $T_1$ to a relatively high value at approximately $T_2$. Following this rapid increase the rate of deceleration remains substantially constant for a relatively long period.

Figure 6:
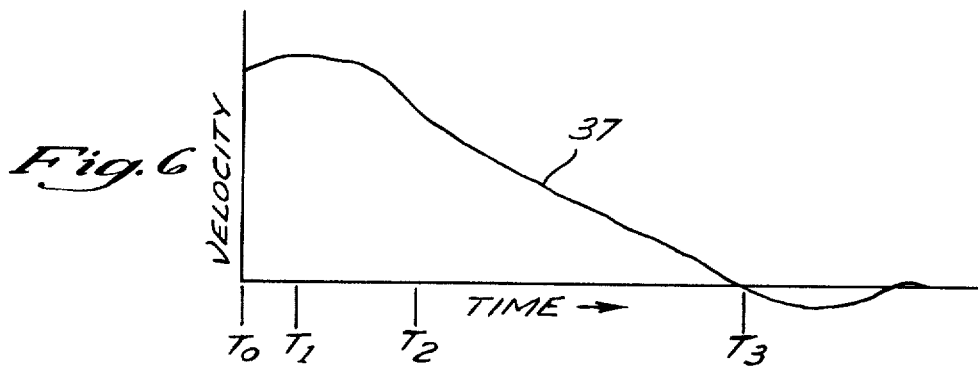
FIG. 6 is a diagrammatic curve representing instantaneous velocity of the hammer as a function of time.

FIG. 6 illustrates the instantaneous velocity of the hammer 24. A velocity curve 37 of FIG. 6 may be derived by integrating the deceleration curve 36 as is understood by those skilled in the art. This integration process may be carried out by suitable electronic circuitry with the results visually displayed for example on a screen, film or other type of recording medium or displayed in digital form. The hammer velocity remains substantially constant during the period of initial contact between $T_0$ and $T_1$ and then gradually decreases to zero at $T_3$. At the instant $T_3$ the velocity of the hammer is substantially zero and the surrounding soil is substantially motionless. At this point in time $T_3$, then, the resistance of the soil to further penetration by the mass of concrete is without velocity dependent effects so that the resistance of the soil at this instant reflects the static load bearing capacity of the concrete mass and surrounding soil in a static condition.

The initial concrete charge 22 is assumed to be moving in unison with the hammer 24 so that the deceleration of the concrete is the same as that of the hammer 24. The resistance of the soil may be computed by using the relationship $R = M_t A_d$, where R is the resistance of the soil, $M_t$ is the combined total mass of the hammer 24 and concrete charge 22, and $A_d$ is the deceleration of the hammer 24 and concrete 22 at zero velocity ($T_3$). An adjustment factor to account for nonaxial concrete motion, plastic and dynamic effects may be added in that relationship. The necessary computation can be done by use of electronic analog and/or digital circuitry in the field, or by utilizing permanent records or a screen display on an oscilloscope manually. According to this relationship, the resistance R is calculated as the product of the combined mass and the deceleration at zero velocity. The load bearing capacity of the concrete charge 22 is equal to the resistance R by the law of reaction forces. The hammer 24 may be repeatedly dropped on the initial charge 22 of concrete until it is sufficiently embedded in the high bearing value stratum 13 such that the calculated resistance R reaches the required value. It may be necessary to add additional amounts of concrete to fill the volume of soil displaced in the formation of the bulb 32. In such a case, the total mass of the concrete being driven at one time must be determined and used in the governing equation for resistance R given above.

After an adequate base 32 is driven, the casing 10 is elevated a limited predetermined distance from its initial lowermost position by lifting cables 39. An additional charge of concrete is introduced into the casing and the hammer is again dropped to set this additional material. Ideally, this concrete material is struck with enough energy to cause it to expand or bulge slightly laterally of the casing 10 to produce an annular ring or enlargement 42 between the base 32 and lower end 16 of the casing. The lateral or radial resistance of the soil surrounding the annular enlargement 42 may be determined by the above resistance formula using the value of hammer deceleration during the blow in question and the total mass of concrete in motion. This latter concrete mass may be assumed to be that contained in the casing and that in the zone just below the casing end 16 from which the casing is lifted. The volume of concrete in this zone evacuated by the casing 10 is determined by the diameter of the casing and the last incremental height to which it was raised.

This procedure may be repeated by raising the casing in incremental steps and adding suitable charges of concrete to develop a series of additional enlargements 43 along the length of the pile shaft. The casing 10 is eventually completely withdrawn from the soil 11 and the enlargements 43 are produced from the base 32 to the ground level 18. The enlargements 43 cooperate with the surrounding soil 11 to improve the friction resistance of the pile over that which would result from a pile having a smooth cylindrical exterior. It is understood that, as in normal practice in forming concrete piles, all additional charges of concrete are provided and all hammer blows are performed prior to setting, i.e., appreciable hardening of the initial and such subsequent additional charges.

In certain situations it may be desirable to provide an intermediate rigid mass between the hammer and concrete such as a piston or mandrel. In such a case, the mass of this rigid member must be added to the mass of the hammer and concrete in the computation of the resistance R. In the instances where it is not necessary to provide the casing 10 to support the hole 14 from collapse prior to filling with concrete it is possible to form a pile without the casing by placing concrete directly into the hole. The bulb 32 and enlargements 42, 43 may be formed in the manner described but without the control in their placement provided with the casing.

Although a preferred embodiment of the invention is illustrated and described, it is to be understood that various rearrangements and alternative procedures and steps may be resorted to without departing from the scope of the invention disclosed and claimed herein. To such rearrangements belongs the instrumentation of the hammer that drives the casing in the same way as it is done with the hammer that forces the concrete to form a bulb. Measurements and data analysis are then similar and a pile capacity for a pile without bulb is found.

What is claimed is:

1. A method of determining the static load capacity of a concrete pile during its construction comprising the steps of providing deceleration measuring means on a hammer of predetermined mass, charging a hole with a known mass of concrete, dropping the hammer on the charge of concrete to drive the concrete into a base of the hole, measuring the deceleration of the hammer with the decelerometer, integrating the deceleration to determine the velocity of the hammer, calculating the resistance of the soil by computing the product of the combined mass of the hammer and the charge of concrete and the value of the deceleration of the hammer substantially at the point of zero velocity, when a desirable resistance value is obtained after one or more hammer blows adding an additional charge or charges of concrete before said first-mentioned charge of concrete has set and performing the steps of determining the soil resistance set forth in relation to the first-mentioned charge with at least one successive charge.

2. A method as set forth in claim 1 wherein a removable casing is positioned in the hole prior to initial formation of the pile and successive charges of concrete of known mass are introduced into the hole, each charge being driven by a separate hammer blow, and the steps of determining soil resistance set forth in relation to the first charge being performed with each successive charge.

3. A method of constructing a concrete pile of known load bearing capacity comprising the steps of placing a pipe casing into the soil at the desired pile location to a depth immediately above the desired position of the pile base, providing a first charge of concrete at the lower end of the pipe casing, providing a drop hammer with decelerometer means rigidly mounted thereon to measure deceleration of the hammer after impact with the first charge of concrete, dropping the hammer on the concrete charge to drive the charge axially downward and radially outwardly of the pipe end to form a pile base, integrating the deceleration of the hammer to determine its velocity, determining the static resistance of the first concrete charge by calculating the product of the sum of the mass of the hammer and the mass of the first charge of concrete and the deceleration of the hammer substantially at the point of zero velocity, redropping the hammer on the concrete charge with or without introducing an additional mass of concrete, recalculating the resistance of the pile base by computing the product of the mass of the hammer and total mass of concrete introduced into the casing and the deceleration of the redropped hammer, repeating the process of redropping the hammer with or without introduction of additional concrete mass until a desired resistance value is achieved.

4. The method as set forth in claim 3 wherein subsequent to reaching the desired resistance value the pipe casing is elevated from its initial position a predetermined limited distance, an additional new mass of concrete is introduced in the pipe casing, and the steps of dropping the hammer onto the additional new concrete to determine a new value of resistance is repeated until a desired resistance is achieved.

5. A method of determining the static load capacity of a pile according to claim 1 wherein said combined mass also includes a casing and a bottom plug.

* * * * *